United States Patent [19]
Ortiz et al.

[11] Patent Number: 5,130,997
[45] Date of Patent: Jul. 14, 1992

[54] MEDICAL LASER APPARATUS, HIGH POWERED RED LASER USED IN SAME, AND LASER RESONATOR WITH NON-LINEAR OUTPUT

[75] Inventors: Mark V. Ortiz, San Jose; Dirk J. Kuizenga, Sunnyvale, both of Calif.

[73] Assignee: Laserscope, San Jose, Calif.

[21] Appl. No.: 631,697

[22] Filed: Dec. 18, 1990

[51] Int. Cl.$^5$ .............................................. H01S 3/10
[52] U.S. Cl. ...................................... 372/21; 372/22; 372/105; 372/108
[58] Field of Search ...................... 372/21, 22, 41, 108, 372/105, 99, 34; 359/326, 328

[56] References Cited

U.S. PATENT DOCUMENTS

| | | | |
|---|---|---|---|
| 3,719,414 | 3/1973 | Wentz | 372/105 |
| 3,949,323 | 4/1976 | Bierlein et al. | 332/7.51 |
| 4,048,515 | 9/1977 | Liu | 372/108 |
| 4,231,838 | 11/1980 | Gier | 156/600 |
| 4,272,733 | 6/1981 | Walling et al. | 372/41 |
| 4,637,026 | 1/1987 | Liu | 372/21 |
| 4,852,115 | 7/1989 | Viherkoski | 372/108 |
| 4,907,235 | 3/1990 | Kuizenga | 372/21 |

OTHER PUBLICATIONS

Koechner; Solid-State Laser Engineering, 2d Ed., Springer-Verlag, (Jan. 1988), pp. 4577–518, particularly pp. 514–518.

Kleinman, et al.; Second-Harmonic Generation of Light with Double Refraction; Physical Review; vol. 137, No. 4a, Feb., 1965, pp. A1305–A1320.

Kleinman, et al.; Second-Harmonic Generation of Light By Focused Laser Beams, Physical Review, vol. 145, No. 1, May, 1966, pp. 338–346.

Ballman, et al., Growth of Potassium Titanyl Phosphate (KTP) From Molten Tungstate Melts, Journal of Crystal Growth 75 (Jan. 1986) 390–394, Elsevier Science Publishers B.V., North-Holland, Amsterdam (see p. 394, column 1).

Gettemy, et al., Some Optical Properties of KTP, LiIO$_3$, and LiNbO$_3$, IEEE Journal of Quantum Electronics, vol. 24, No. 11, Nov., 1988.

*Primary Examiner*—Georgia Y. Epps
*Attorney, Agent, or Firm*—Fliesler, Dubb, Meyer & Lovejoy

[57] ABSTRACT

A laser system generates suitable laser power for use in photodynamic therapy, and particularly photodynamic therapy using dyes which undergo desired photodynamic reactions at 659 mm, i.e., Purpurin. The laser system generates a red output power of greater than 4 watts. For the therapeutic applications, a means for delivering the red beam to therapeutic sites is provided. The laser system provides for a frequency doubled solid-state laser system in which the non-linear birefringent crystal used to provide frequency doubling is mounted adjacent a flat mirror whereby losses due to walkoff of the beam caused by the crystal are minimized. The laser resonant cavity defined by one flat and one other mirror, which may be stabilized by means, such as thermal lensing in the solid-state gain medium, inside the cavity. A frequency doubled Nd:YAG rod in such cavity tuned to 1.319 microns with a KTP frequency doubling crystal for generates an output beam at 0.659 microns via type II phase matching required for photodynamic therapy in conjunction with a suitable PDT compound or dye.

26 Claims, 5 Drawing Sheets

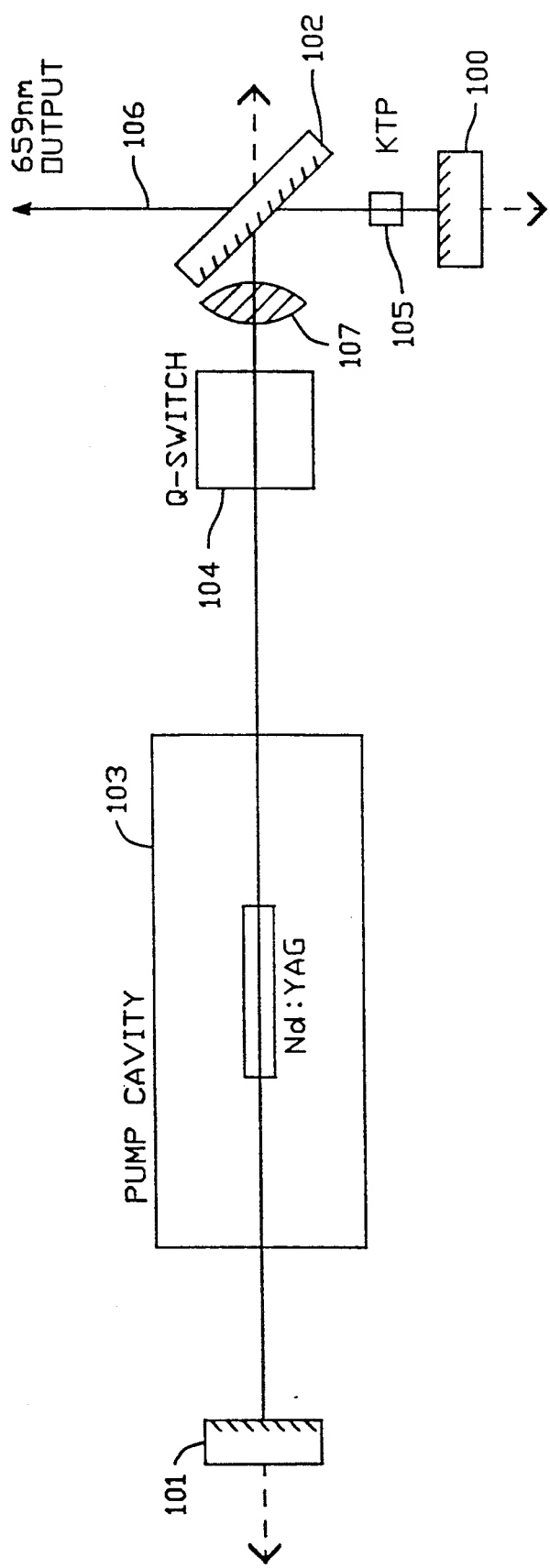
FIG.—6

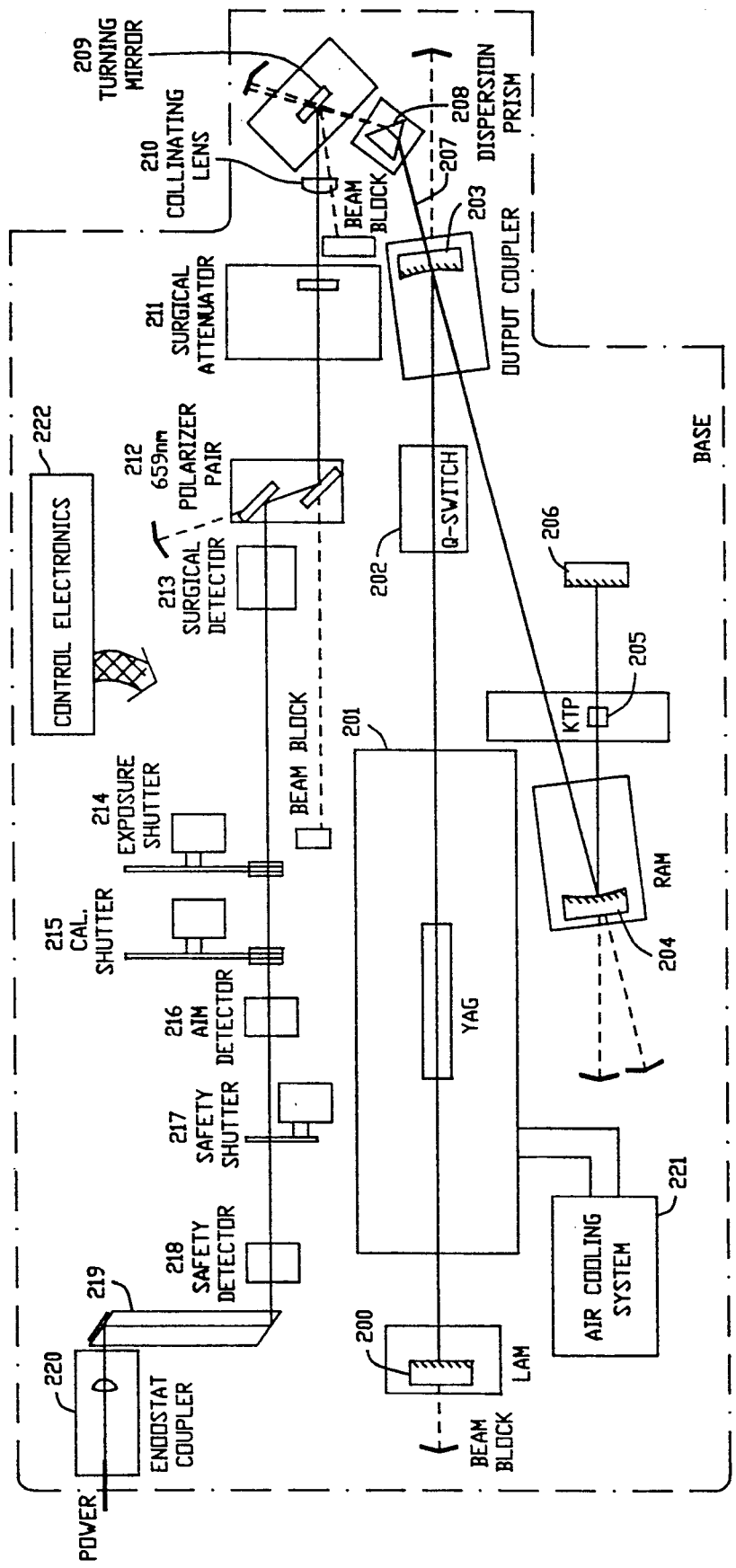
FIG.—7

MEDICAL LASER APPARATUS, HIGH POWERED RED LASER USED IN SAME, AND LASER RESONATOR WITH NON-LINEAR OUTPUT

FIELD OF THE INVENTION

The present invention relates to laser systems for generating output beams having a wavelength different from the cavity mode, such as those including crystals for providing sum frequency generation within the cavity, and more particularly to such systems generating a high powered second harmonic red output beam. Furthermore, the present invention relates to systems and methods for providing laser energy for medical applications requiring red output beams, i.e., photodynamic therapy (PDT), dermatology, etc.

BACKGROUND OF THE INVENTION

Many therapeutic uses of lasers are based on photo-reactions of tissues, or dyes which are absorbed preferentially by only diseased tissue, that are wavelength specific. For instance, certain types of dyes absorb a specific wavelength of light. Photo-reaction by-products in tissues contaminated with specific dyes, as well as the absorbed heat itself, are used for therapeutic purposes. For instance, cancerous tissue treated with Purpurin is irradiated with 659 nanometer red laser light, to cause singlet oxygen byproducts, which attack the cancerous tissue.

Reliable and practical lasers which generate light at a specific wavelength with sufficient power to achieve the therapeutic objectives present complicated design problems. Gain media in practical laser systems are limited to relatively few lasing wavelengths. Therefore, a non-linear optic element is needed to generate wavelengths outside the gain profile of the laser media. Specifically, non-linear optical crystals, such as KDP, KD*P, KTP, LBO, BBO, and others, are used for harmonic generation in resonant cavities, as is well known in the art. For a discussion of harmonic generation in solid state laser systems, see Koechner, "SOLID-STATE LASER ENGINEERING", 2d Edition, Springer-Verlag, 1988, pp. 477–518, and particularly pp. 514–518. See, also, Kleinman, et al.. "SECOND-HARMONIC GENERATION OF LIGHT BY FOCUSED LASER BEAMS", PHYSICAL REVIEW, Vol. 145, No. 1, May 1966, pp. 338–346; and Boyd, et al., "SECOND-HARMONIC GENERATION OF LIGHT WITH DOUBLE REFRACTION", PHYSICAL REVIEW, Vol. 137, No. 4a, Feb. 1965, pp. A1305-A1320.

The amount of power available in these laser systems using harmonic generation has been limited by a variety of parameters. For instance, the anisotropic crystals used for harmonic generation are birefringent. It may happen that this birefringence causes the extraordinary and ordinary ("e" and "o" beams in a uniaxial crystal) or simply orthogonally polarized beams (since both are considered to be extraordinary in the case of a biaxial crystal) to diverge within the crystal. Because overlap of the orthogonally polarized beams at the lasing wavelength in the crystal is necessary for non-linear interaction between the two orthogonal electric fields which will result in power produced at the desired sum frequency output wavelength, wavelengths which have a high divergence angle, or walkoff, within the crystals have not been efficiently generated in the past.

Therefore, for practical laser systems in the prior art, it has been difficult to generate laser beams at certain important wavelengths with sufficient power to achieve therapeutic purposes. For instance, red lasers having an output power greater than about 2 watts have not been practical. The only system known by the Applicants which produces a power in the red greater than 2 watts are large krypton gas ion lasers. These laser systems are impractical for therapeutic purposes because of their immense size and the high power requirements. Further, these systems only generate red outputs at specific wavelengths with very small powers. Only when all the red lines of a prior art krypton gas ion laser are combined, is the maximum power known by Applicant to have been produced repeatedly about 4½ watts. However, such high power gas lasers are not practical for medical applications.

In practical laser systems, such as frequency doubled Nd:YAG lasers, the maximum output power available has been about 2 watts. This limited amount of output power, which is further attenuated by systems for delivering the beam to therapeutic sites, limits the speed with which a desired dosage of radiation can be administered. Therefore, certain therapies take an unnecessarily long period of time to accomplish.

For instance, certain photodynamic therapy is based on depositing certain dyes in the tissue to be treated. As mentioned above, a dye known to have useful photoreactions at 659 mm is known as Purpurin. When Purpurin is preferentially taken up at cancer cell sites, and irradiated with red light at essentially 659 nanometers in wavelength, therapeutic effects such as singlet oxygen generation and heating on the cancerous tissue are achieved. However, the prior art systems have been unable to deliver light at 659 wavelengths at greater than about 2 watts. Therefore, the speed with which this Purpurin therapy or other therapy requiring red laser light can be accomplished has been significantly limited. It will be appreciated that dyes other than Purpurin can be employed.

Accordingly, it is desirable to provide a practical laser system which provides significant output power at practical pumping powers using non-linear optics, such as used in second harmonic generation. More particularly, it is desirable to provide an output beam in the red having a power of greater than 4 watts for many therapeutic purposes.

SUMMARY OF THE INVENTION

The present invention provides an apparatus which generates suitable laser power to achieve photodynamic therapy, and particularly for photodynamic therapy based on Purpurin compounds (and other dyes which undergo photoreactions when exposed to 659 mm radiation). According to another aspect of the invention, a practical laser system is provided which generates a red output power of greater than 4 watts. For the therapeutic applications, a means for delivering controlled dosages of the red beam to therapeutic sites is provided.

The laser system described and claimed herein includes several aspects of invention. The first aspect includes providing for a frequency-doubled solid state laser system, in which the non-linear crystal used to provide frequency doubling causes divergence of orthogonally polarized components of the cavity mode of greater than about 20 milliradians, and is mounted adjacent a flat mirror whereby walkoff effects of the beam caused by the crystal are minimized. In a related aspect, the invention provides for use of KTP or its isomorphs as the non-linear crystal, aligned for type II or type III phase matching outside of the x - y plane, such as may be required for certain useful frequencies of light.

According to another aspect, the laser system is based on utilization of a frequency doubled Nd:YAG rod in a cavity tuned to 1.319 microns with a KTP frequency doubling crystal for generating an output beam at 0.659 microns (659 nanometers). The cavity is defined by at least two mirrors, whereby one is flat, stabilized within a range of pump power by thermal lensing of the Nd:YAG rod. Further, a means, such as an optical relay, within the cavity is provided for controlling the power density within the KTP crystal to optimize harmonic generation.

According to yet another aspect of the present invention, the laser system of the present invention is air cooled, which makes it particularly suited to the therapeutic applications, which typically take place at installations that are not equipped to handle extremely high power laser systems requiring water cooling and special electrical power service.

Other aspects and advantages of the present invention will be seen upon review of the figures, the detailed description, and the claims which follow.

BRIEF DESCRIPTION OF THE FIGURES

FIG. 6 is a schematic diagram of an alternative embodiment of the laser system according to the present invention.

FIG. 7 is a schematic diagram of an apparatus providing illuminating energy to a therapeutic site according to the present invention.

DESCRIPTION OF THE PREFERRED EMBODIMENTS

A detailed description of preferred embodiments of the present invention is provided with reference to the figures. The figures show preferred and alternative resonant cavity designs for generating greater than 4 watts of red output power with reference to FIGS. 1 through 6. FIG. 7 illustrates a medical laser system including a laser and an apparatus for delivering a controlled dosage of the laser output power to therapeutic sites.

Figure 1:
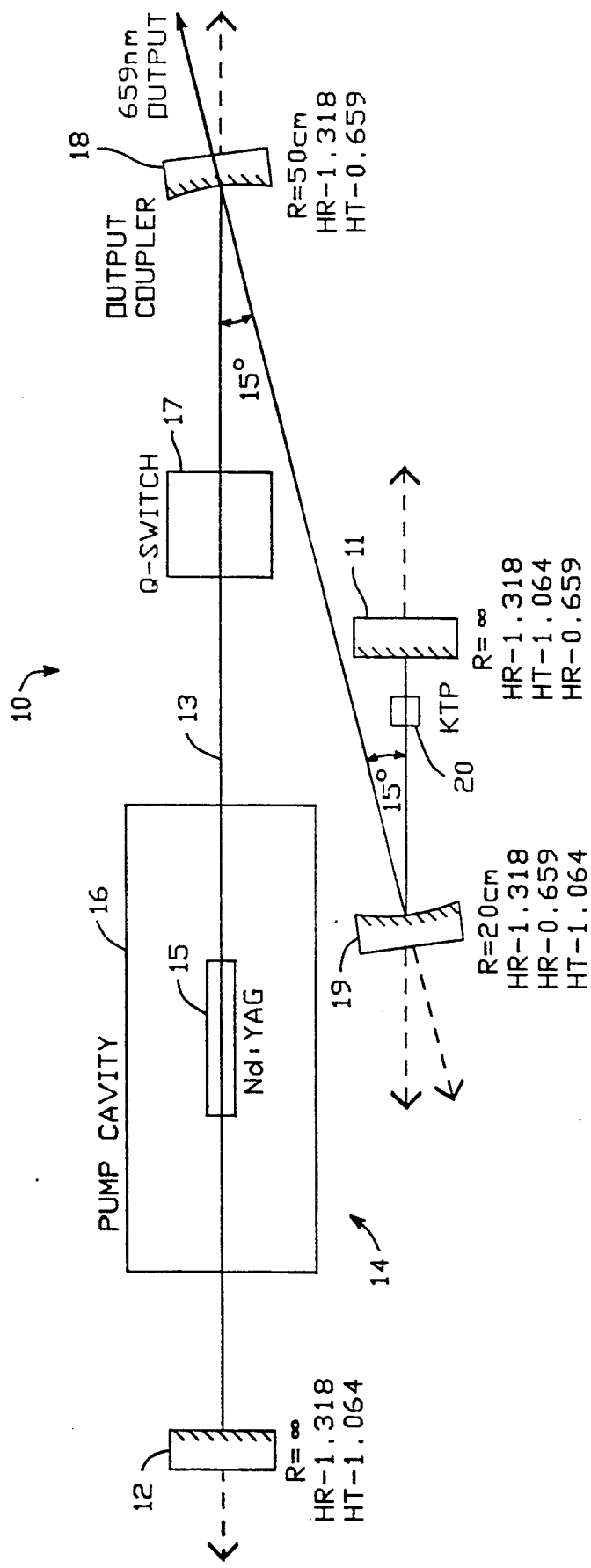
FIG. 1 is a diagram of a laser system according to the present invention.

As illustrated in FIG. 1, the laser system, according to a preferred embodiment of the present invention, includes a resonant cavity referred to generally by the reference number 10, which is limited by a first flat mirror 11 and a second flat mirror 12. An optical path 13 within the resonant cavity is defined. Along the optical path 13 are mounted a gain medium, referred to generally by the reference number 14, which in the preferred system, comprises a rod of Nd:YAG 15 mounted in a pump cavity 16. Adjacent the gain medium 14 is a Q-switch 17. Typically, the Q-switch is an acousto-optic Q-switch, as is known in the art.

An output coupler 18 is mounted adjacent the Q-switch 17. The output coupler comprises a curved, dichroic mirror which is highly reflective at the cavity mode wavelength and highly transmissive at the desired output wavelength.

At the output coupler, the optical path 13 is folded at an angle of 15° towards the turning mirror 19. This turning mirror then folds the optical path through a non-linear optical crystal 20, such as a crystal of KTP. Finally, mounted adjacent to KTP crystal is the first flat mirror 11.

In operation, the laser is Q-switched at 5 kHz with 25 watts of RF power at a carrier frequency of 27.2 MHz and a gate duration of about 6 microseconds. The Nd:YAG rod 15 has a diameter of 4 millimeters and is 79 mm long. It is doped with 1.1% (atomic) neodymium. The pump cavity 16 includes a continuous wave krypton gas arc lamp having a 5 mm bore diameter operating at 113 volts at 40 amps.

The first flat mirror 11 is highly reflective at 1.319 microns, highly transmissive at 1.064 microns, and highly reflective at 0.659 microns. The second flat mirror 12 is highly reflective at 1.319 microns and highly transmissive at 1.064 microns. The output coupler has a 50 cm radius of curvature and is highly reflective at 1.319 microns and highly transmissive at 0.659 microns. Finally, the turning mirror 19 has a 20 cm radius of curvature and is highly reflective at both 1.319 microns and 0.659 microns, while being highly transmissive at 1.064 microns.

The optical path is about 41.61 inches long, with a length between the second flat mirror 12 and the output coupler 18 about 23.232 inches, the length between output coupler 18 and turning mirror 19 about 13.78 inches, and the length between the turning mirror 19 and the flat mirror 11 about 4.598 inches. The KTP crystal 20 is mounted about one inch from the flat mirror 11. The KTP crystal in the illustrated embodiment has a cross section of 3 mm by 3 mm and a length of 5 mm.

The Nd:YAG rod 15 provides thermal lensing at the predetermined pumping power range, sufficient to stabilize the resonant cavity.

The combination of the output coupler 18 and the turning mirror 19 provide an optical relay which demagnifies the beam at the output of the Nd:YAG rod by a factor of 2.5 at the center line of the KTP crystal. This optical relay controls the intensity of the laser radiation in the KTP crystal for a wide range of pump powers. This technique is described in detail in U.S. Pat. No. 4,907,235, invented by Kuizenga, issued Mar. 6, 1990, which is incorporated by reference as if fully set forth herein.

The KTP crystal (hydrothermal and flux grown material has been used with equal success) is used to frequency double the 1.319 micron line in Nd:YAG, which is selected via the laser mirrors. The KTP crystal is oriented for Type II frequency doubling at the Nd:YAG 1.319 micron line. In the preferred system, the KTP crystal is oriented for phase matching in the x - z plane at about $\theta_z = 60°$ and $\phi_x = 0°$, within manufacturing tolerances. The divergence of the orthogonally polarized beams in the KTP crystal at this wavelength and at this orientation is approximately 44 milliradians. In an alternative embodiment, the KTP crystal can be oriented for phase matching in the y - z plane at about $\theta_z = 50.2°$ and $\phi_x = 90°$. At this orientation, the divergence is about 45 milliradians. Other orientations for type II or for type III doubling in the x - z or y - z planes are also possible for generating other wavelengths in KTP.

Typical applications of the KTP crystal for frequency doubling are oriented for phase matching in the x - y plane. For instance, frequency doubled Nd:YAG lasers for doubling the 1.064 micron line use KTP oriented for frequency doubling in the x - y plane. Those frequencies which can be phase matched in the x - y plane suffer very small divergence of the orthogonally polarized components of the cavity mode within the crystal. Therefore, the walkoff for KTP frequency doubling based on phase matching in the x - y plane is minimal. When one moves to frequencies in which phase matching must be accomplished outside the x - y plane, such as in the x - z or y - z planes, the difference in index of refraction for the orthogonally polarized components of the beam become greater, and result in much greater divergence.

For instance, the divergence angle for frequency doubling the 1064 line in a Nd:YAG system, using KTP phase matching in the x - y plane is about 4 milliradians. Thus, in these systems, the design of the mirror adjacent the KTP crystal is dictated by parameters other than the walkoff in the KTP. Therefore, the mirror can be a curved mirror in order to optimize cavity stability or for other reasons. However, when phase matching in the x - z or y - z planes of KTP crystals, the present invention becomes critical to reduce the effects of walkoff, maintain a stable cavity, and provide significant conversion efficiency.

The x, y, and z axes referred to herein correspond, as is conventional in the art, to the a, b, and c crystallographic axes of the non-linear crystals, such that a, b, and c are mapped to x, y, and z according to the index of refraction n, and in which $n_z > n_y > n_x$.

Figure 2:
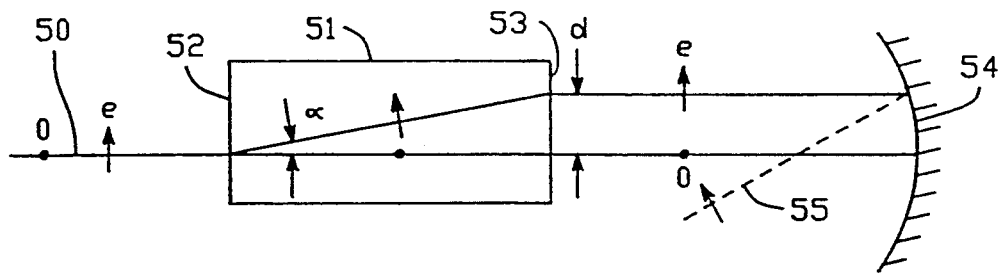
FIG. 2 is a heuristic diagram illustrating the problem of walkoff in the non-linear crystal in prior art laser systems.

FIG. 2 illustrates the effect of walkoff in a curved mirror system, typical of the prior art. As can be seen, the incoming beam 50 is an unpolarized cavity mode having orthogonally polarized components, labelled "e" and "o". Upon entering the KTP crystal 51 at entry face 52, the "o" and "e" beams diverge at angle α. At the exit face 53, the beams are separated by or have "walked off" a distance d. When they leave the crystal 51, they propagate along parallel paths separated by the distance d. When the beams strike the curved mirror 54, they will be reflected at different angles. In order to optimize cavity performance, the curved mirror is aligned so that either the "e" or the "o" beam strikes the center of the mirror and is retroreflected back through the KTP crystal 51. However, because of the walkoff distance d, the other beam ("e" in the Figure) is reflected by the curved mirror along a non-parallel path. In extreme conditions of walkoff, this non-parallel path 55, leaves the resonant cavity altogether.

The resulting loss of one of the orthogonally polarized components of the cavity mode significantly increases the lasing threshold of the cavity. Also, because of the extreme divergence, double pass through the KTP crystal for second harmonic conversion cannot be accomplished. In prior art systems, such as frequency doubling at the 1064 line an Nd:YAG with KTP with phase matching in the x - y plane, the divergence angle α is small enough that the walkoff distance d becomes insignificant for most practical laser systems. This is true because the angle at which the off-center component of the beam reflects off the mirror 54 is sufficiently small that a significant portion of the off-center component is coupled back into the resonant cavity.

Figure 3:
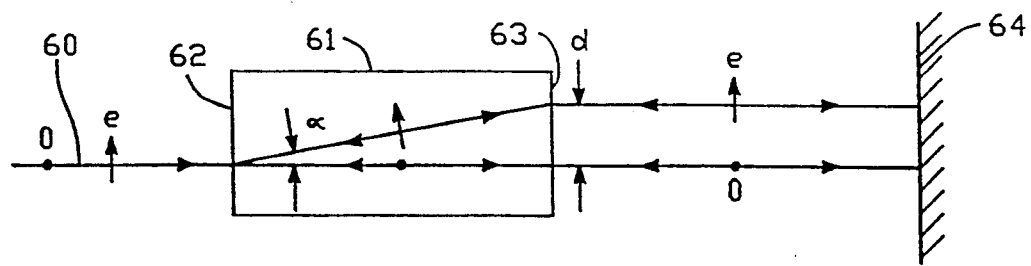
FIG. 3 is a heuristic diagram illustrating the use of flat mirrors with non-linear crystals exhibiting walkoff.

According to the present invention, the curved mirror 54 is replaced by a flat mirror as illustrated in FIG. 3. As can be seen in FIG. 3, the incoming beam 60 enters the KTP crystal 6 at entry face 62. The "e" and "o" components diverge at angle α, which results in a walkoff of the distance d at the exit face 63 of the crystal 61. When the components of the beam strike flat mirror 64, they are retroreflected back into the crystal 61. At the face 63 of crystal 61, the beams retrace their paths and recombine at face 62 of the crystal 61. Thus, both the components of the lasing wavelength are retained in the cavity mode. This results in efficient double pass second harmonic generation, as well as a decrease in the lasing threshold of the system and higher conversion efficiency.

The utilization of a flat mirror 64 however, causes certain design limitations on the resonant cavity as a whole. For example, in the case of strong lensing solid state laser media, i.e., Nd:YAG, the position of the flat mirror 64 should be placed as close as possible to the KTP crystal.

For a beam diameter at the KTP crystal of about 1.5 millimeters, which is generated by de-magnifying the beam of about 3.8 mm provided at the output of the 4 mm Nd:YAG rod, with 44 milliradian divergence through a 5 mm KTP crystal, walkoff is about 22 mm in the KTP crystal. This maintains significant overlap of the beams and efficient second harmonic generation.

Figure 4:
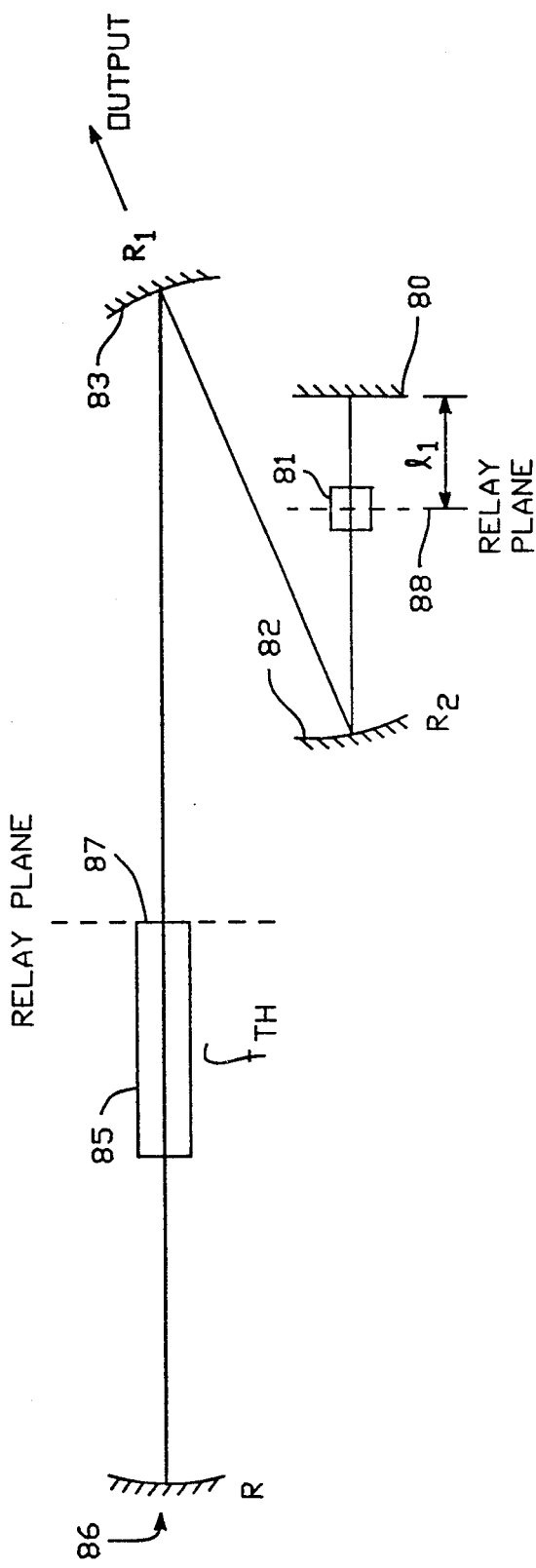
FIG. 4 is a schematic diagram of the preferred laser resonator of the present invention.
Figure 5:
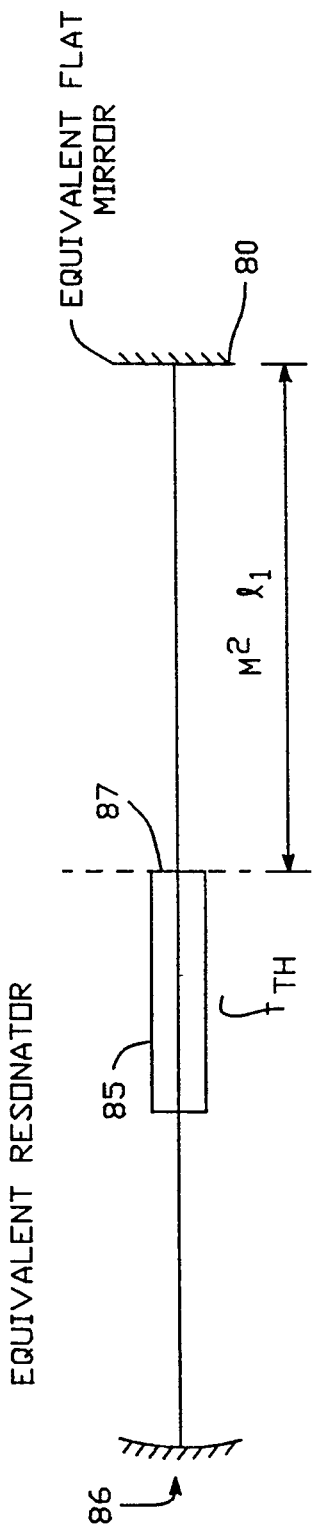
FIG. 5 illustrates the equivalent resonator to that of FIG. 4, in view of the optical relay in the resonator.

FIGS. 4 and 5 are used to illustrate this feature of the present invention. In particular, FIG. 4 is a schematic diagram of a resonator such as that illustrated in FIG. 1. The resonator includes a first flat mirror 80, a KTP crystal 81, and a pair of curved mirrors 82 and 83 which act as an optical relay having magnification m. Magnification m is determined by the radius of curvature R1 of mirror 83 divided by radius of curvature R2 of mirror 82.

The resonant cavity is completed by an Nd:YAG gain medium 85 and a mirror 86. The mirror 86 may be a flat mirror, or a curved mirror, as suits the needs of a particular design. A flat mirror is used in the preferred system.

The optical relay formed by mirrors 82 and 83 is set up so that a first relay plane sits on face 87 of the YAG rod 85 and a second relay plane sits at the center line 88 of the KTP crystal 81.

Because of the effect of the relay, the equivalent resonator is illustrated in FIG. 5. As can be seen, the effective resonator will lave a distance between the face 87 of the YAG rod 85 and the flat mirror 80 equal to $m^2 l_1$ where m is the magnification of the optical relay and $l_1$, (see FIG. 4), is the distance between the center line 88 of the KTP crystal 81 and the flat mirror 80. Therefore, the range of stability of the resonator is determined by $m^2 l_1$ as a function of the focal length $f_{th}$ caused by thermal lensing of the Nd:YAG rod 85. Because greater stability at higher pump powers is achieved with a shorter optical cavity, it is necessary that the distance $l_1$ be minimized for high pumping power. In fact, very small increases in the distance $l_1$ have a large effect on the range of pump powers in which the cavity will be stable.

In the preferred system, the non-linear crystal is KTP, which is oriented for phase matching at a frequency which cannot be phase matched in the x - y plane, such as the 1.319 line of the Nd:YAG. When phase matching outside the x - y plane, the divergence of the orthogonally polarized beams in the crystal becomes significant. Thus, the divergence of beams which are phase matched outside the x - y plane is typically greater than about 20 milliradians. As mentioned above, for the 1.319 micron line, the divergence angle for phase matching in the x - z and y - z planes is 44 and 45 milliradians, respectively.

At these large divergence angles, a resonant cavity having a flat mirror positioned as close as possible to the non-linear crystal as described above is critical for efficient conversion to the second harmonic, and to achieve significant output powers.

Although the preferred non-linear crystal consists of KTP, isomorphs of KTP could be used in other systems as suits the needs of particular designs. KTP and its isomorphs are described in detail in U.S. Pat. No. 3,949,323, to Bierlein, et al., and U.S. Pat. No. 4,231,838, to Gier. Such patents are incorporated by reference for a teaching of properties of KTP and its isomorphs.

Further, other non-linear crystals which exhibit birefringence sufficient for phase matching in the near infrared (a range up to around 2 microns) could be used beneficially in laser systems according to the present invention where walkoff in the non-linear crystal becomes significant, such as in systems where the divergence angle causes significant cavity losses at the fundamental mode in curved mirror systems. This typically occurs when the walkoff angle becomes greater than about 20 milliradians.

FIG. 6 illustrates an alternative resonator design according to the present invention. In FIG. 6, the resonant cavity consists of a first flat mirror 100 and a second flat mirror 10 arranged in an L-shaped optical path. A flat output coupler 102 is provided, which is highly reflective at the cavity mode and transmissive at the frequency-doubled mode. Also, there is an intracavity lens 107 (which would optimally be coated to minimize losses at the cavity mode and second harmonic) which provides sufficiently high laser radiation intensity in the non-linear optical crystal to provide efficient frequency conversion. Thus, the laser system includes a pump cavity 103 which includes an Nd:YAG rod, and a Q-switch 104 between the flat output coupler 102 and the flat mirror 101. The cavity mode is reflected by the output coupler 102 through KTP crystal 105 into flat mirror 100 where it is retroreflected back through the KTP crystal 105 and the output coupler 102. The frequency-doubled component supplies an output beam along path 106 and the cavity mode is reflected back through the Q-switch and the Nd:YAG rod in the pump cavity 103. Because mirror 100 is flat, the overlap of the orthogonally polarized beams in the KTP crystal is optimized. Alternatively, it can be said that the effect of walkoff in the KTP crystal is minimized.

The systems of FIGS. 1 and 6 are based on frequency-doubling Nd:YAG lasers using KTP frequency-doubling crystals. As recognized by those skilled in the art a wide variety of other gain media and frequency doubling crystals could be used. A description of representative materials and doubling crystals is provided in the before referenced textbook by Koechner.

FIG. 7 illustrates medical laser systems, such as used in photodynamic therapy and other medical procedures. This apparatus includes the laser resonator illustrated in FIG. 1 based on flat mirror 200, pump cavity 201, Q-switch 202, output coupler 203, turning mirror 204, KTP crystal 205, and flat mirror 206. The output beam is provided along a path 207 through a dispersion prism 208. From prism 208, a turning mirror 209 reflects the desired 659 nanometer output into collimating lens 210. The collimated 659 nanometer beam is directed into a surgical attenuator 211 used to control the amount of dosage provided to the therapeutic site. A 659 nanometer polarizer pair 212 receives the output of the surgical attenuator and directs it through surgical detector 213. The beam is then provided through other components including an exposure shutter 214, a calibration shutter 215, an aim detector 216, a safety shutter 217, a safety detector 218, turning mirror assembly 219, and an endostat coupler 220. The endostat coupler couples the beam into a fiber used to deliver the controlled dosage to the therapeutic site on the human or other subject.

As illustrated schematically, the system is air cooled, using air cooling system 221. This system is described in detail in prior co-pending U.S. patent application entitled "AIR COOLING OF FREQUENCY DOUBLED SOLID STATE LASER FOR SURGICAL APPLICATIONS". Ser. No. 07/598,485, which was filed on Oct. 16, 1990, invented by Scott A. Davenport, Mark V. Ortiz, Linda Chen, and Dirk J. Kuizenga. The invention described in this application was owned at the time of invention, is currently owned by the same Assignee as the present application, and is incorporated by reference for teaching the air cooling system of the present invention. As described in said co-pending application, the control electronics 222 is involved in the air cooling, and controls all the elements in the system for delivering the output beam to the fiber.

The present invention apparatus provides the ability to perform laser therapy by providing an output of 659 nanometers in the red at sufficient power to achieve desired dosages required for certain therapeutic results in a reasonable amount of time. For instance, this laser can be used for many dermatology related procedures.

The present invention is particularly suited for photodynamic therapy based on Purpurin compounds. Thus, according to the present invention, a human or other mammal can be treated according to the following method. First, the human or other mammal is treated with the Purpurin compound to contaminate cancerous tissue with Purpurin. Second, an ultraviolet source is used at the suspected cancer invaded site for diagnosing the extent of the invasion, as the cancerous tissue which has preferentially taken up the dye will fluoresce Third, the laser is provided which generates an output beam having a power of greater than 4 watts at the wavelength of 659 nanometers in the red. Next, a controlled dosage of the beam is scanned over the cancerous tissue to induce a reaction with the Purpurin which destroys the tumor or tissue in which the dye molecules have localized. Both the chemical and thermal aspects of the treatment are beneficial components.

A significant feature provided by the present laser system is that the high powers of the light at the specific wavelength required for Purpurin therapy is provided which has been unavailable in the prior art. At least 4 watts power is critical for practical therapeutic procedures.

Accordingly, a laser system has been provided which generates significant powers in frequency-doubled laser systems. Particularly, the present invention provides high powered output at 659 nanometers which is required for many medical procedures. Using this laser system, medical therapeutic procedures can be accomplished more rapidly and, therefore, for less cost.

The laser of the preferred system has generated an average power of over 7 watts at a lamp current of about 30 amps (about 3 kilowatts of electrical pump power). It is expected that using a greater diameter YAG rod will increase output power at 659 nanometers, providing the ability to perform many other medical applications beyond photodynamic therapy with appropriate drugs or dyes.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. A laser system for generating an output beam at wavelength $\lambda 2$, comprising:
    a resonant cavity tuned for a cavity mode at wavelength $\lambda 1$ and having a laser threshold, defining an optical path and having at least a first flat mirror reflective at wavelength $\lambda 1$;
    a gain medium, mounted in the optical path within the resonant cavity, providing optical gain at wavelength $\lambda 1$ in response to pump energy;
    means, coupled with the gain medium, for supplying pump energy to the gain medium;
    a nonlinear crystal in the optical path within the resonant cavity producing an interaction of light at the wavelength $\lambda 1$ to generate light at the wavelength $\lambda 2$, wherein the crystal causes divergence of greater than 20 milliradians of orthogonally polarized components of the light at the wavelength $\lambda 1$, and wherein the nonlinear crystal is mounted adjacent the flat mirror so that nonlinear interaction of the cavity mode in the nonlinear crystal is increased and the laser threshold of the resonant cavity is decreased; and
    means, mounted in the optical path within the resonant cavity, for extracting light at the wavelength $\lambda 2$ to provide the output beam.

2. The laser system of claim 1, wherein the nonlinear crystal exhibits birefringence sufficient for phase matching in the near infrared.

3. The laser system of claim 1, wherein the nonlinear crystal comprises one of a group including KTP and its isomorphs oriented for phase matching outside of the x-y plane.

4. The laser system of claim 1, wherein the resonant cavity includes:
    a second flat mirror mounted perpendicular to the optical path so that the length of the optical path is determined by a distance between the first and second flat mirrors; and the gain medium comprises:
    a solid state gain material exhibiting thermal lensing so that in a predetermined range of pump power the resonant cavity is stabilized.

5. The laser system of claim 4, wherein the solid state material comprises Nd:YAG, and wherein $\lambda 1$ equals essentially 1.319 microns and $\lambda 2$ equals essentially 0.659 microns.

6. The laser system of claim 1, wherein the resonant cavity includes:
    an optical relay, mounted in the optical path within the resonant cavity and having magnification m, for controlling the intensity of the cavity mode within the birefringent crystal for a predetermined range of pump power;
    and the gain medium comprises:
    a solid state gain material exhibiting thermal lensing so that in the predetermined range of pump power the resonant cavity is stabilized; and wherein
    stability of the resonant cavity is determined by distance 1 between the non-linear crystal and the first flat mirror.

7. The laser system of claim 6, wherein the solid state material comprises Nd:YAG, and wherein $\lambda 1$ equals essentially 1.319 microns and $\lambda 2$ equals essentially 0.659 microns.

8. The laser system of claim 5, wherein the means for extracting provides an output beam of more than 4 watts at wavelength 0.659 microns.

9. A laser system for generating an output beam at wavelength $\lambda/2$, comprising:
    a resonant cavity tuned for a cavity mode at wavelength $\lambda$ and having a laser threshold, having at least a first flat mirror reflective at wavelength $\lambda$, the resonant cavity defining an optical path;
    a solid state gain medium, mounted in the optical path within the resonant cavity, providing optical gain at wavelength $\lambda$ in response to pump energy, the medium exhibiting thermal lensing so that in a predetermined range of pump power the resonant cavity is stabilized;
    means, coupled with the gain medium, for supplying pump energy to the gain medium in the predetermined range;
    a nonlinear crystal, comprising one of the group including KTP and its isomorphs, in the optical path within the resonant cavity and oriented for phase matching outside of the x-y plane to generate light at the wavelength $\lambda/2$, wherein the crystal causes divergence of orthogonally polarized components of the light at the wavelength $\lambda$, and wherein the nonlinear crystal is mounted adjacent the flat mirror so that nonlinear interaction of the cavity mode in the nonlinear crystal is increased and the laser threshold of the resonant cavity is decreased;
    means, mounted in the optical path within the resonant cavity, for controlling the intensity of the cavity mode within the birefringent crystal for the predetermined range of pump power; and
    means, mounted in the optical path within the resonant cavity, for extracting light at the wavelength $\lambda/2$ to provide the output beam.

10. The laser system of claim 9, wherein $\lambda$ equals essentially 1.319 microns and $\lambda/2$ equals essentially 0.659 microns.

11. The laser system of claim 10, wherein the means for extracting provides an output beam of more than 4 watts at wavelength 0.659 microns.

12. A laser system for generating a red output beam of over 4 watts, comprising:
    a resonant cavity tuned for a cavity mode at wavelength $\lambda$, defining an optical path;

a solid state gain medium, mounted in the optical path within the resonant cavity, providing optical gain at wavelength λ in response to pump energy;

means, coupled with the gain medium, for supplying pump energy to the gain medium;

a nonlinear crystal mounted in the optical path within the resonant cavity producing an interaction of light at the wavelength λ to generate red light; and means, mounted in the optical path within the resonant cavity, for extracting over 4 watts red light to provide the output beam.

13. The laser system of claim 12, wherein the nonlinear crystal comprises one of a group including KTP and its isomorphs oriented for phase matching outside of the x-y plane.

14. The laser system of claim 12, wherein the nonlinear crystal causes divergence within the crystal of greater than 20 milliradians of orthogonally polarized components of the light at the wavelength λ; and resonant cavity includes at least a first flat mirror mounted in the optical path adjacent the nonlinear crystal so that nonlinear interaction of the orthogonally polarized components of the cavity mode is increased.

15. A medical laser system, comprising:
a laser generating a red output beam including means for generating an output power of over 4 watts in the red output beam;

means, coupled with the laser, for delivering a controlled dosage of the red output beam to a therapeutic site.

16. The laser system of claim 15, wherein said laser comprises:
a resonant cavity tuned for a cavity mode at wavelength λ, defining an optical path;

a gain medium, mounted in the optical path within the resonant cavity, providing optical gain at wavelength λ in response to pump energy;

means, coupled with the gain medium, for supplying pump energy to the gain medium;

a nonlinear crystal mounted in the optical path within the resonant cavity producing an interaction of light at the wavelength λ to generate red light; and means, mounted in the optical path within the resonant cavity, for extracting over 4 watts red light to provide the output beam.

17. The laser system of claim 16, wherein the nonlinear crystal causes divergence within the crystal of greater than 20 milliradians of orthogonally polarized components of the light at the wavelength λ; and resonant cavity includes at least a first flat mirror mounted in the optical path adjacent the nonlinear crystal so that nonlinear interaction of the orthogonally polarized components of the cavity mode is increased.

18. The laser system of claim 17, wherein the resonant cavity includes:
a second flat mirror mounted perpendicular to the optical path so that the length of the optical path is determined by distance between the first and second flat mirrors; and means, mounted in the optical path; for stabilizing the resonant cavity.

19. The laser system of claim 17, wherein the resonant cavity includes:
an optical relay, mounted in the optical path within the resonant cavity having magnification m, for controlling the intensity of the cavity mode within the birefringent crystal for a predetermined range of pump power;

and the gain medium comprises:

a solid state gain material exhibiting thermal lensing so that in the predetermined range of pump power the resonant cavity is stabilized; and wherein stability of the resonant cavity is determined by a distance 1 between the first flat mirror and the non-linear crystal.

20. The laser system of claim 19, wherein the solid state material comprises Nd:YAG, and wherein λ equals essentially 1.319 microns and the red output beam has a wavelength of essentially 0.659 microns.

21. The laser system of claim 19, wherein the nonlinear crystal comprises one of a group including KTP and its isomorphs oriented for phase matching outside of the x-y plane.

22. The laser system of claim 15, further including means for air cooling the system.

23. An apparatus of providing illuminating energy to a therapeutic site sensitive to light at 659 nanometers wavelength in photodynamic therapy, comprising:
a frequency-doubled solid state laser providing an output beam having a wavelength of approximately 659 nanometers and an output power of more than 4 watts; and means, coupled with the laser, for delivering a controlled dosage of the output beam to a therapeutic site.

24. The apparatus of claim 23, further including means for air cooling the system.

25. The apparatus of claim 24, wherein the laser comprises:
a resonant cavity tuned for a cavity mode at a cavity mode wavelength of approximately 1319 nanometers and having a laser threshold, having at least a first flat mirror reflective at the cavity mode wavelength and a second mirror reflective at the cavity mode wavelength defining an optical path;

a gain medium comprising Nd:YAG, mounted in the optical path within the resonant cavity, providing optical gain at wavelength of approximately 1319 nanometers in response to pump energy, the Nd:YAG exhibiting thermal lensing so that in a predetermined range of pump power the resonant cavity is stabilized;

means, coupled with the gain medium, for supplying pump energy to the gain medium in the predetermined range;

a nonlinear crystal in the optical path within the resonant cavity producing an interaction of light at the cavity mode wavelength to generate light at the wavelength of approximately 659 nanometers, wherein the crystal causes divergence of orthogonally polarized components of the light at the cavity mode wavelength, and wherein the nonlinear crystal is mounted adjacent the flat mirror so that nonlinear interaction of the cavity mode in the nonlinear crystal is increased and the laser threshold of the resonant cavity is decreased;

means, mounted in the optical path within the resonant cavity, for controlling the intensity of the cavity mode within the nonlinear crystal for the predetermined range of pump power; and means, mounted in the optical path within the resonant cavity, for extracting light at the wavelength of approximately 659 nanometers to provide the output beam.

26. The laser system of claim 25, wherein the nonlinear crystal comprises one of a group including KTP and its isomorphs oriented for phase matching outside of the x-y plane.

* * * * *